(12) United States Patent
Pellechia (10) Patent No.: US 10,151,710 B2
(45) Date of Patent: Dec. 11, 2018

(54) PORTABLE INDUSTRIAL RADIOGRAPHY APPARATUS

(71) Applicant: Peltec Services, Inc., Darlington, SC (US)

(72) Inventor: Richard Pellechia, Florence, SC (US)

( * ) Notice: Subject to any disclaimer, the term of this patent is extended or adjusted under 35 U.S.C. 154(b) by 0 days.

(21) Appl. No.: 14/803,369

(22) Filed: Jul. 20, 2015

(65) Prior Publication Data

US 2016/0021725 A1 Jan. 21, 2016

Related U.S. Application Data

(60) Provisional application No. 62/026,160, filed on Jul. 18, 2014.

(51) Int. Cl.
| | |
|---|---|
| *G01N 23/04* | (2018.01) |
| *G01N 23/06* | (2018.01) |
| *G01N 23/083* | (2018.01) |
| *G01N 23/087* | (2018.01) |
| *H05G 1/02* | (2006.01) |

(52) U.S. Cl.
CPC ............. *G01N 23/04* (2013.01); *G01N 23/06* (2013.01); *G01N 23/083* (2013.01); *G01N 23/087* (2013.01); *G01N 2223/301* (2013.01); *G01N 2223/308* (2013.01); *H05G 1/025* (2013.01)

(58) Field of Classification Search
CPC ....... A61B 6/4405; A61B 6/44; A61B 6/4411; A61B 6/4429; A61B 6/4452; A61B 6/4458; G01N 23/04; G01N 23/06; G01N 23/083; G01N 23/087

USPC ................... 378/196–198, 51, 53–55, 58, 62
See application file for complete search history.

(56) References Cited

U.S. PATENT DOCUMENTS

| | | | | |
|---|---|---|---|---|
| 1,877,690 | A * | 9/1932 | Russell | A61B 6/14 248/174 |
| 2,232,014 | A * | 2/1941 | Simon | A61B 6/447 378/190 |
| 2,360,036 | A * | 10/1944 | Boucher | G01N 23/18 378/201 |
| 2,588,124 | A * | 3/1952 | Kizaur | A61B 6/00 378/177 |
| 2,607,012 | A * | 8/1952 | Siebert | G01M 3/005 248/292.13 |
| 3,644,735 | A * | 2/1972 | Vandervelden | A61B 6/14 378/197 |
| 3,790,805 | A | 2/1974 | Foderaro | |
| 4,166,602 | A * | 9/1979 | Nilsen | A61B 6/447 248/280.11 |
| 4,202,355 | A * | 5/1980 | Loeffler | A61B 5/107 600/587 |

(Continued)

*Primary Examiner* — Allen C. Ho
(74) *Attorney, Agent, or Firm* — Matthew M. Googe; Robinson IP Law, PLLC (57) ABSTRACT

A portable industrial radiography apparatus is provided for radiographic non-destructive testing. The portable industrial radiography apparatus includes a support frame, an upright support member attached to the support frame, an elongate lift arm including a first end and a second end, wherein the elongate lift arm is pivotally attached to the upright support member adjacent the second end of the lift arm, an x-ray tube attached to the first end of the elongate lift arm, and a linear actuator positioned between the support frame and the lift arm for manipulating a position of the x-ray tube attached to the first end of the elongate lift arm.

20 Claims, 9 Drawing Sheets

(56) References Cited

U.S. PATENT DOCUMENTS

| | | | | |
|---|---|---|---|---|
| 4,442,536 A * | 4/1984 | Schaefer | A61B 6/4429 | 378/26 |
| 4,503,552 A * | 3/1985 | Miyahara | A61B 6/4429 | 378/196 |
| 4,727,564 A * | 2/1988 | Mekker | A61B 6/4283 | 378/176 |
| 4,752,948 A * | 6/1988 | MacMahon | A61B 6/4405 | 378/193 |
| 4,805,202 A * | 2/1989 | Deucher | A61B 6/00 | 378/195 |
| 4,875,228 A * | 10/1989 | Archer | A61B 6/102 | 378/197 |
| 4,912,754 A * | 3/1990 | Van Steenburg | A61B 6/0442 | 378/179 |
| 4,993,057 A * | 2/1991 | Runnells | A61B 6/4429 | 378/193 |
| 5,283,823 A * | 2/1994 | Morris | A61B 6/4405 | 378/193 |
| 5,388,142 A | 2/1995 | Morris | | |
| 5,428,660 A * | 6/1995 | Daniel, Jr. | A61B 6/14 | 378/167 |
| 5,586,162 A * | 12/1996 | Grichnik | A61B 6/4405 | 378/189 |
| 5,997,176 A * | 12/1999 | Fairleigh | A61B 6/501 | 378/195 |
| 6,131,690 A * | 10/2000 | Galando | A61B 6/4405 | 180/19.1 |
| 6,374,937 B1 * | 4/2002 | Galando | A61B 6/4405 | 180/19.1 |
| 6,496,558 B2 * | 12/2002 | Graumann | A61B 6/0478 | 378/197 |
| 7,048,439 B2 * | 5/2006 | Hubner | A61B 6/105 | 248/288.51 |
| 7,175,345 B2 * | 2/2007 | Kantor | H05G 1/04 | 378/197 |
| 7,319,738 B2 * | 1/2008 | Lasiuk | G01N 23/04 | 378/198 |
| 7,360,262 B2 * | 4/2008 | Mowery | A61G 7/1015 | 5/83.1 |
| 7,429,130 B2 * | 9/2008 | Malucelli | A61B 6/14 | 378/197 |
| 7,502,444 B2 * | 3/2009 | Marar | A61B 6/10 | 378/101 |
| 7,628,537 B2 * | 12/2009 | Schulze-Ganzlin | A61B 6/145 | 378/170 |
| 7,785,006 B2 * | 8/2010 | Kim | A61B 6/4441 | 378/181 |
| 7,905,658 B2 * | 3/2011 | Groß | A61B 6/4458 | 378/193 |
| 7,938,579 B2 * | 5/2011 | Groß | A61B 6/4458 | 378/197 |
| 7,972,061 B2 * | 7/2011 | Groß | A61B 6/4488 | 378/197 |
| 8,376,612 B2 * | 2/2013 | Takae | A61B 6/4283 | 378/198 |
| 8,419,276 B2 * | 4/2013 | Oda | A61B 6/4283 | 378/198 |
| 8,430,564 B2 * | 4/2013 | Simmons | A61B 6/4405 | 378/197 |
| 8,459,868 B2 * | 6/2013 | Boomgaarden | A61B 6/4405 | 378/198 |
| 8,465,203 B2 * | 6/2013 | Barker | A61B 6/4405 | 378/197 |
| 8,568,028 B2 | 10/2013 | Wendlandt et al. | | |
| 8,622,614 B2 * | 1/2014 | Carmichael | A61B 6/4266 | 378/198 |
| 8,636,410 B2 * | 1/2014 | Yao | A61B 6/4405 | 378/197 |
| 8,657,494 B2 * | 2/2014 | Müller | A61B 6/4441 | 378/189 |
| 8,662,536 B2 * | 3/2014 | Moreno Vallejo | B62B 3/001 | 280/35 |
| 8,672,543 B2 * | 3/2014 | Kralles | A61B 6/4405 | 378/102 |
| 8,678,648 B2 * | 3/2014 | Lalena | A61B 6/4266 | 378/114 |
| 8,678,649 B2 * | 3/2014 | Bechard | A61B 6/00 | 378/198 |
| 8,708,561 B2 * | 4/2014 | Eaves | A61B 6/4233 | 378/198 |
| 8,840,304 B2 * | 9/2014 | Perez Zarate | A61B 6/4405 | 378/197 |
| 8,876,379 B2 * | 11/2014 | DiRisio | A61B 6/447 | 378/193 |
| 8,899,834 B2 * | 12/2014 | Barker | A61B 6/4405 | 250/370.09 |
| 8,961,011 B2 * | 2/2015 | Lalena | A61B 6/4405 | 378/197 |
| 9,055,911 B2 * | 6/2015 | Sakuragi | A61B 6/4429 | |
| 9,101,319 B2 * | 8/2015 | Kojima | A61B 6/4405 | |
| 9,121,805 B2 * | 9/2015 | Omura | A61B 6/4405 | |
| 9,125,611 B2 * | 9/2015 | Eaves | A61B 6/4405 | |
| 9,170,214 B2 * | 10/2015 | Ferren | G01N 23/04 | |
| 9,198,270 B2 * | 11/2015 | Chicchetti | H05G 1/08 | |
| 9,295,438 B2 * | 3/2016 | Omura | A61B 6/4405 | |
| 9,326,747 B2 * | 5/2016 | Omura | A61B 6/4405 | |
| 9,413,961 B2 * | 8/2016 | Welsh | A61B 6/4405 | |
| 9,414,794 B2 * | 8/2016 | Kaku | A61B 6/4405 | |
| 9,414,795 B2 * | 8/2016 | Nakata | A61B 6/4405 | |
| 9,521,984 B2 * | 12/2016 | Moreno Vallejo | A61B 6/4405 | |
| 9,622,716 B2 * | 4/2017 | Jarva | A61B 6/14 | |
| 9,649,074 B2 * | 5/2017 | Simon | A61B 6/025 | |
| 9,693,437 B2 * | 6/2017 | Simmons | G01N 23/04 | |
| 9,693,746 B2 * | 7/2017 | Ancar | A61B 6/08 | |
| 9,730,653 B2 * | 8/2017 | Niizeki | A61B 6/035 | |
| 9,855,446 B2 * | 1/2018 | Chang | A61N 5/1084 | |
| 9,895,559 B2 * | 2/2018 | Chang | A61B 34/30 | |
| 10,058,303 B2 * | 8/2018 | Shimohira | A61B 6/4405 | |
| 10,071,265 B2 * | 9/2018 | Chang | A61B 6/4458 | |
| 2014/0093045 A1 | 4/2014 | Shimada et al. | | |

\* cited by examiner

PORTABLE INDUSTRIAL RADIOGRAPHY APPARATUS

CROSS-REFERENCE TO RELATED APPLICATION

This application claims priority to U.S. Application Ser. No. 62/026,160 to Richard Pellechia entitled "Portable Industrial Radiography Apparatus" which was filed on Jul. 18, 2014, the contents of which are incorporated herein by reference in its entirety.

FIELD

This disclosure relates to the field of industrial radiography. More particularly, this disclosure relates to a portable and reconfigurable industrial radiography device for performing non-destructive testing or examination of an area of interest.

BACKGROUND

Performing industrial radiography or replacing old radiography devices can become an expensive endeavor. Local regulations vary from state to state, and even location to location. A new radiography location may not have all safeties and interlocks required for an x-ray system. Also, positioning an x-ray tube to take an image often requires rigging or fixtures that may be expensive.

For example, systems such as the disclosure of U.S. Pat. No. 5,717,734 describe technology related to microfocus x-ray tubes. However, the system of this disclosure is not capable of being relocated and requires integration with an x-ray vault. While some medical x-ray devices may offer portability, these devices are extremely limited in dose energies. Further, many devices configured for medical use are substantially complex, bulky, and limited in maneuverability of an x-ray portion of the device, and therefore not suitable analyzing a variety of objects in an industrial setting.

What is needed, therefore, is a portable industrial radiography device configured to be easily repositioned and readily adaptable for nondestructive testing or examination of an area of interest.

SUMMARY

The above and other needs are met by a portable industrial radiography apparatus. In one aspect, the portable industrial radiography apparatus includes a support frame, an upright support member attached to the support frame, an elongate lift arm including a first end and a second end, an x-ray tube attached to the first end of the elongate lift arm, and a linear actuator positioned between the support frame and the lift arm for manipulating a position of the x-ray tube attached to the first end of the elongate lift arm. The elongate lift arm is attached to the upright support member at a pivot adjacent the second end of the lift arm.

In one embodiment, the linear actuator is attached to the lift arm at a point between the first end of the elongate lift arm and the pivot. In another embodiment, the lift arm comprises a shaft slidably inserted into a sleeve.

In yet another embodiment, the sleeve supports the shaft with one or more pairs of opposing angled rollers, the opposing angled rollers shaped to conform to a shape of the shaft. In one embodiment, the opposing angled rollers are attached to the sleeve at a bracket, and wherein the opposing angled rollers are attached to the bracket with a fastener extending through each of the opposing angled rollers. In another embodiment, the shaft and sleeve have diamond-shaped cross-sectional areas.

In one embodiment, the portable industrial radiography apparatus further includes an actuator attached to the lift arm adjacent second end of the lift arm wherein the actuator urges the shaft in a direction along a length of the lift arm. In another embodiment, the portable industrial radiography apparatus includes a friction slip ring and set screw positioned between the x-ray tube and lift arm, wherein the friction ring and set screw enable adjustment of the x-ray tube relative to the lift arm.

In yet another embodiment, the upright support member is positioned at an angle of between about 5° and 60° relative to a vertical axis. In one embodiment, the portable industrial radiography apparatus further includes a gusset attached between the upright support member and support frame.

In another embodiment, the portable industrial radiography apparatus includes a housing attached adjacent the upright support member wherein the housing encapsulates the upright support member and pivot. In yet another embodiment, the support frame comprises a first leg, a second leg parallel to the first leg, a first cross member extending perpendicular from the first leg to the second leg, and a second cross member parallel to the first cross member. In one embodiment, the portable industrial radiography apparatus includes an audible area alarm.

In one embodiment, the portable industrial radiography apparatus includes an external chiller in communication with the x-ray tube with one or more hoses, wherein the one or more hoses are attached to the external chiller with a removable coupler.

In another aspect, a portable industrial radiography apparatus is provided including a support frame, an upright support member attached to the support frame, an elongate lift arm including a first end and a second end, an x-ray tube attached to the first end of the elongate lift arm, and a linear actuator positioned between the support frame and the lift arm for manipulating a position of the x-ray tube attached to the first end of the elongate lift arm. The elongate lift arm is attached to the upright support member at a pivot adjacent the second end of the lift arm. The lift arm includes a shaft slidably inserted into a sleeve, the shaft and sleeve having diamond-shaped cross-sectional areas and one or more pairs of opposing angled rollers for supporting the shaft within the sleeve.

In one embodiment, the portable industrial radiography apparatus includes an actuator attached to the lift arm adjacent second end of the lift arm wherein the actuator urges the shaft in a direction along a length of the lift arm. In another embodiment, the shaft and sleeve have diamond-shaped cross-sectional areas.

In yet another embodiment, the portable industrial radiography apparatus includes a friction slip ring and set screw adjacent the x-ray tube.

In one embodiment, the upright support member is positioned at an angle of between about 5° and 60° relative to a vertical axis.

In yet another aspect, a portable industrial radiography apparatus is provided including: a support frame including a first leg, a second leg parallel to the first leg, a first cross member extending perpendicular from the first leg to the second leg, and a second cross member parallel to the first cross member; an upright support member attached to the support frame, the upright support member positioned at an angle of between about 5° and 60° relative to a vertical axis;

an elongate lift arm including a first end and a second end and further including a shaft slidably inserted into a sleeve, the shaft and sleeve having diamond-shaped cross-sectional areas, one or more pairs of opposing angled rollers for supporting the shaft within the sleeve, and an actuator attached to the lift arm adjacent second end of the lift arm wherein the actuator urges the shaft in a direction along a length of the lift arm; an x-ray tube attached to the first end of the elongate lift arm adjacent a friction slip ring and set screw; and a linear actuator positioned between the support frame and the lift arm for manipulating a position of the x-ray tube attached to the first end of the elongate lift arm. The elongate lift arm is attached to the upright support member at a pivot adjacent the second end of the lift arm

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

DETAILED DESCRIPTION

Various terms used herein are intended to have particular meanings. Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

Figure 1:
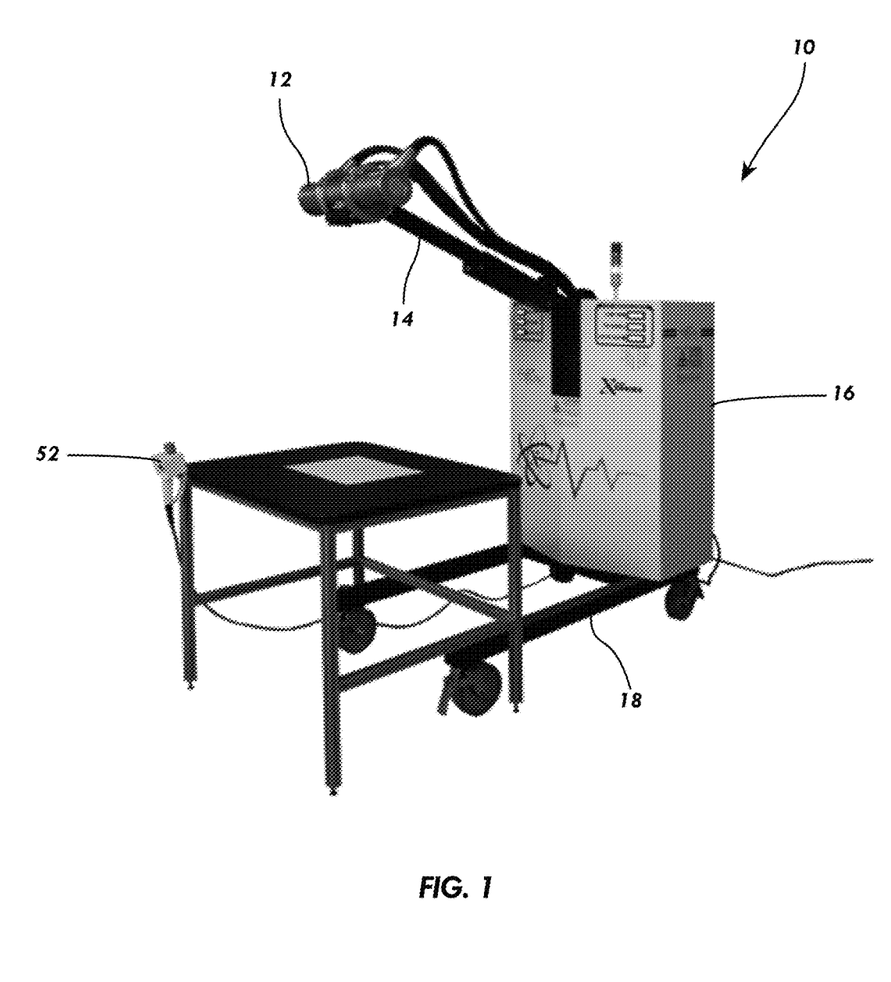
FIG. 1 shows a portable industrial radiography apparatus according to one embodiment of the disclosure.
Figure 2:
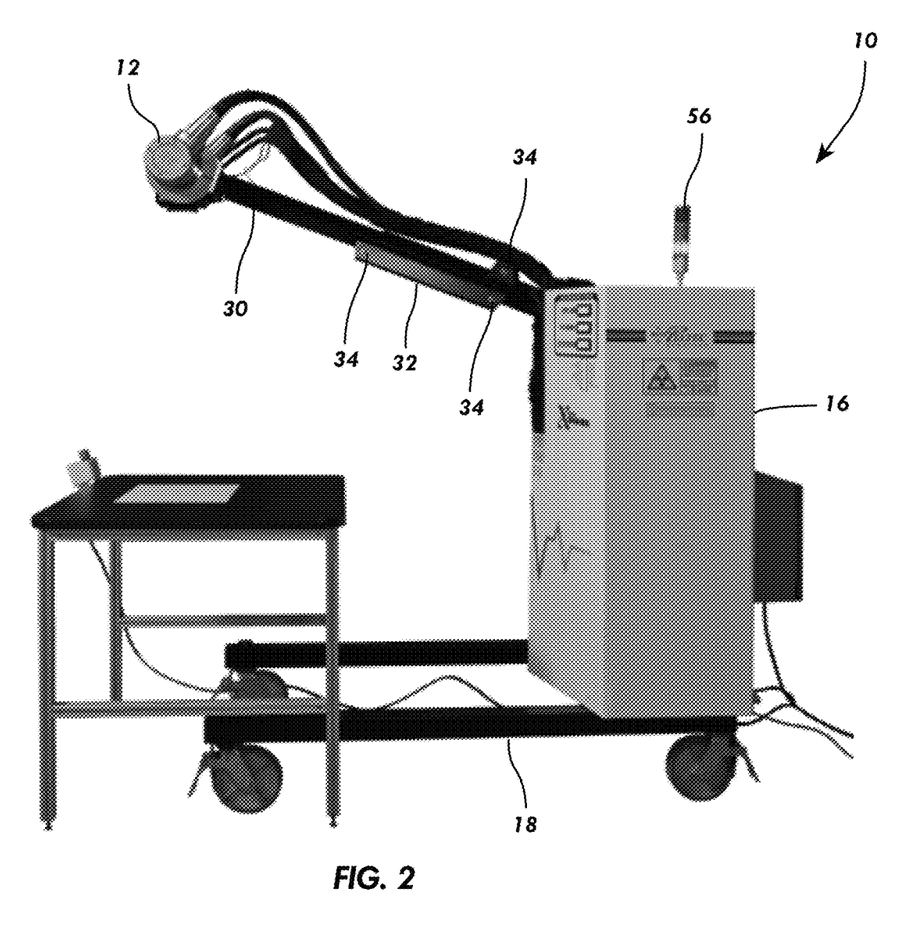
FIG. 2 illustrates a side view of a portable industrial radiography apparatus according to one embodiment of the disclosure.

FIGS. 1 and 2 shows a basic embodiment of a portable industrial radiography apparatus 10 including an x-ray tube 12, a lift arm 14, a housing 16, and a support frame 18. The portable industrial radiography apparatus 10 is substantially compact and portable such that the portable industrial radiography apparatus 10 may be positioned at a desired location, such as a vault or other non-destructive industrial testing setting. The portable industrial radiography apparatus 10 is substantially self-contained in that the portable industrial radiography apparatus 10 includes necessary power supply components, safeties, and interlocks for operation of the portable industrial radiography apparatus 10 for radiographic non-destructive industrial testing.

The x-ray tube 12 is preferably formed of an industrial x-ray tube having a desired voltage. For example, the x-ray tube 12 may be selected from one of 70 kV, 100 kV, 160 kV, 225 kV, 320 kV, 450 kV, 600 kV, and other voltages of available industrial x-ray devices. The x-ray tube 12 may further be formed of a x-ray accelerator head, and other various industrial scanners such as gamma cameras.

Figure 3:
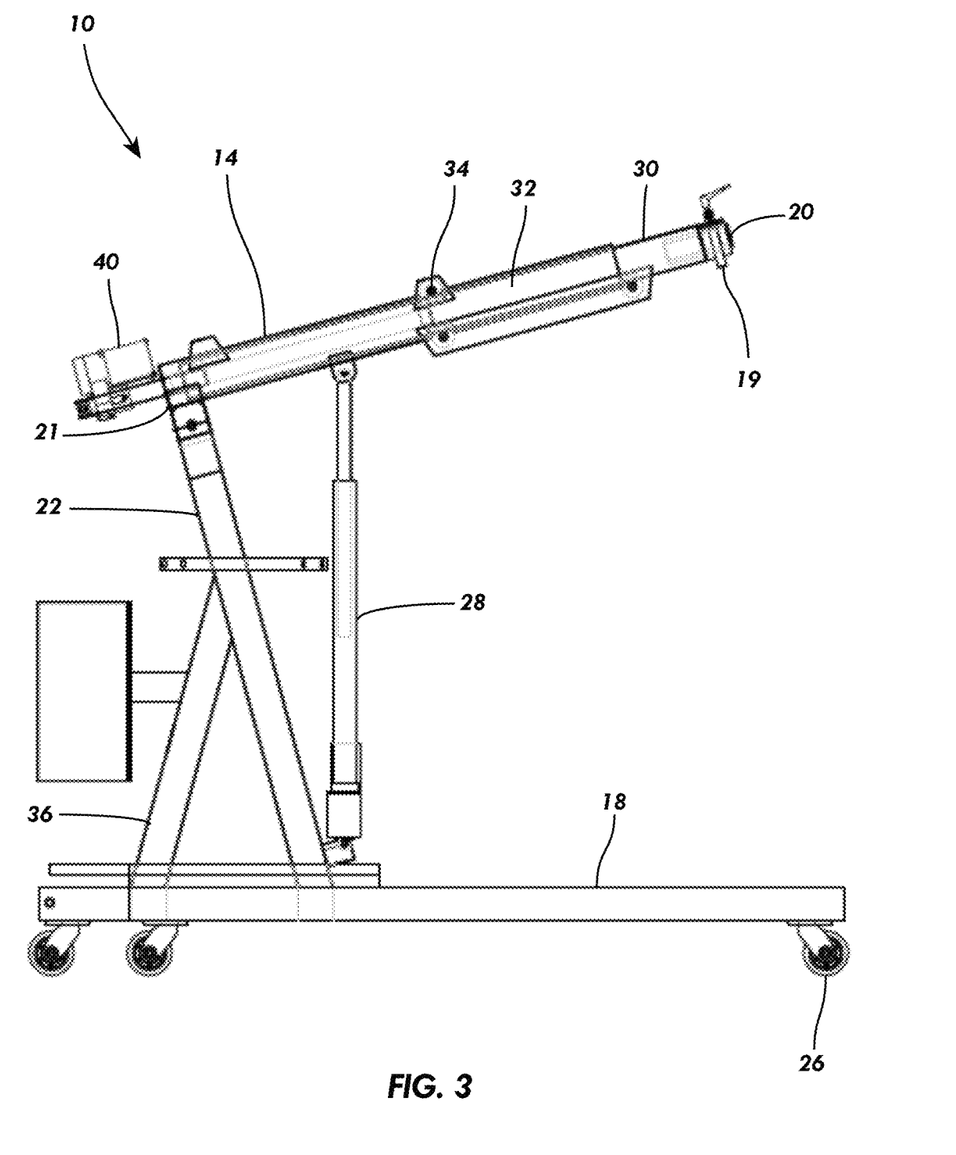
FIG. 3 illustrates a schematic side view of a portable industrial radiography apparatus according to one embodiment of the disclosure.

Referring now to FIG. 3, the x-ray tube 12 (FIG. 1) is attached to a first end 20 of the lift arm 14. The x-ray tube 12 is preferably pivotally attached to the lift arm 14 such that an orientation of the x-ray tube 12 is adjustable relative to a position of the lift arm 14, allowing the x-ray tube 12 to rotate between a substantially vertical position and a substantially horizontal position. A friction slip ring and set screw 19 or other like device maintains the x-ray tube 12 in a desired rotated position relative to the first end 20 of the lift arm 14. Pivotally attaching x-ray tube 12 to the end 20 of the lift arm 14 allows the x-ray tube 12 to provide angled views of an industrial object of interest during non-destructive testing ("NDT"). In one embodiment, a yaw, pitch, and roll of the x-ray tube 12 is adjustable relative to the lift arm 14.

FIG. 3 illustrates the portable industrial radiography apparatus 10 without the normally attached housing 16. As shown in FIG. 3, an upright support member 22 supports the lift arm 14 at a pivot 24 adjacent a second end 21 of the lift arm 14. A gusset 26 supports the upright support member 22 at an angle of between about 5° and 60° relative to a vertical axis and is attached between the upright support member 22 and the support frame 18.

The portable radiography apparatus 10 further includes a linear actuator 28 attached to the support frame 18 adjacent the upright support member 22. The linear actuator 28 attaches to the lift arm 14 at a point between the first end 20 and the second end 21, and preferably at a point nearer to the second end 21 and pivot 24. Examples of suitable linear actuators include mechanical (such as a "screw" or "cam" linear actuator), hydraulic, pneumatic, electro-mechanical, linear motor, and other like actuators.

Figure 4:
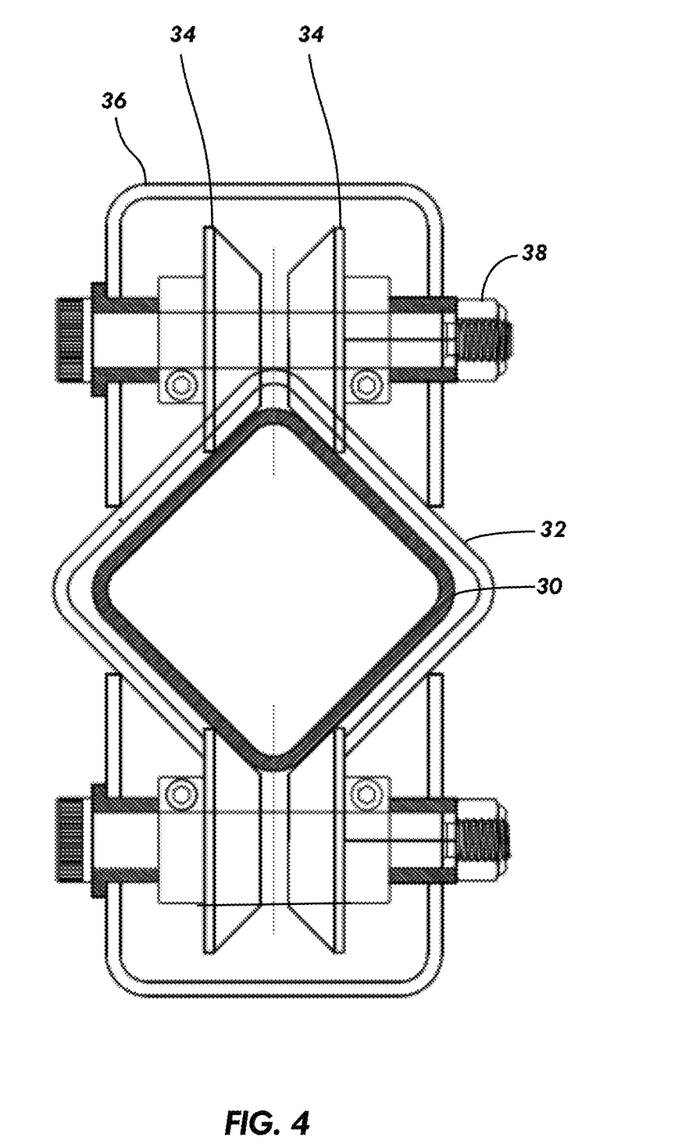
FIG. 4 is a cross-sectional schematic view of a lift arm of a portable industrial radiography apparatus according to one embodiment of the disclosure.
Figure 5:
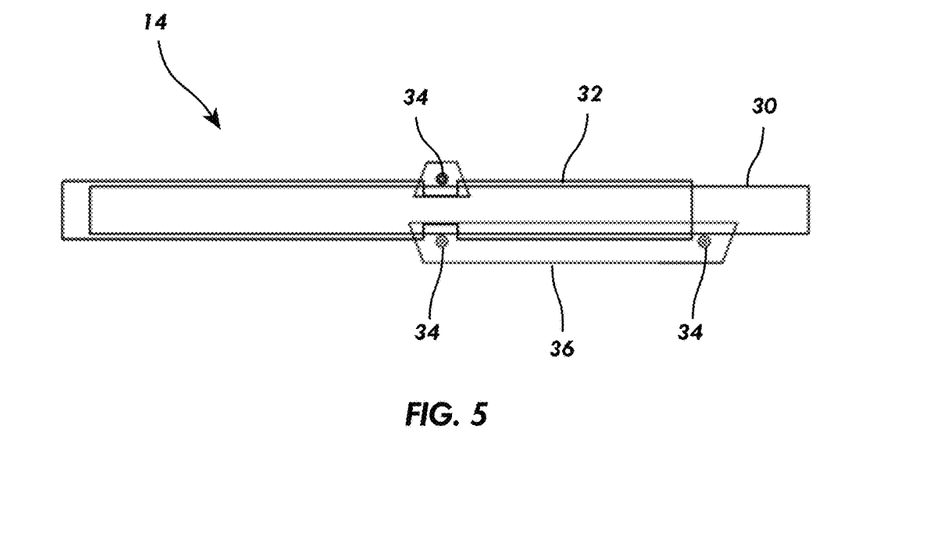
FIG. 5 is a schematic side view of a lift arm of a portable industrial radiography apparatus according to one embodiment of the disclosure.
Figure 6:
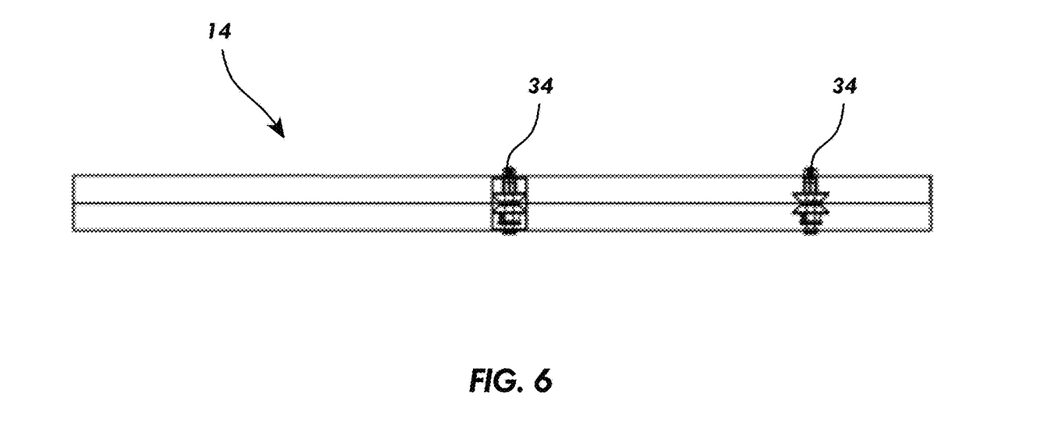
FIG. 6 is a schematic bottom view of a lift arm of a portable industrial radiography apparatus according to one embodiment of the disclosure.

Referring again to FIG. 2, the lift arm 14 telescopes to adjust a position of the x-ray tube 12 along an axis along a length of the lift arm 14. Referring now to FIGS. 4-6, the lift arm 14 includes a shaft 30 slidably inserted into a sleeve 32. FIG. 4 illustrates a cross-sectional view along a length of the lift arm 14. The shaft 30 and sleeve 32 preferably have corresponding diamond-shaped cross-sectional areas with substantially rounded corners. Pairs opposing angled rollers 34 are attached to a bracket 36 surrounding the sleeve 32 and are positioned adjacent a top and bottom of the shaft 30. The angled rollers 34 rotate about a fastener 38 extending through the bracket 36 and angled rollers 34.

The angled rollers 34 are shaped to substantially conform to an exterior of the diamond-shaped shaft 30 and to substantially support a weight of the shaft 30 and attached x-ray tube 12. As shown in FIG. 2, the pairs of angled rollers 34 support the shaft 30 adjacent both a top and bottom of the shaft 30 along a length of the lift arm 14 such that the angled rollers 34 support a weight of the x-ray tube 12 while allowing a length of the lift arm 14 to be slidably adjusted as the shaft 30 slides with respect to the sleeve 32.

While the above description contemplates the shaft 30 and sleeve 32 having a diamond-shaped cross sectional area, in alternative embodiments the shaft 30 and sleeve 32 may have alternative shapes such as circular or oval cross-sectional areas. In alternative embodiments, the pair of opposing angled rollers 34 have a profile shaped to substantially contact and support the shaft 30.

Referring again to FIG. 3, an actuator 40 attached adjacent the second end 21 of the lift arm 14 urges the shaft 30 along a length of the lift arm 14. The actuator may be formed of a linear motor or other like mechanism for inducing linear movement of the shaft 30. The actuator 40 urges the shaft 30 in a direction along a length of the lift arm 14, which is supported by the opposing angled rollers, thereby a linear position of the x-ray tube 12 adjacent the first end 20 of the lift arm 14 to be adjusted.

Figure 7:
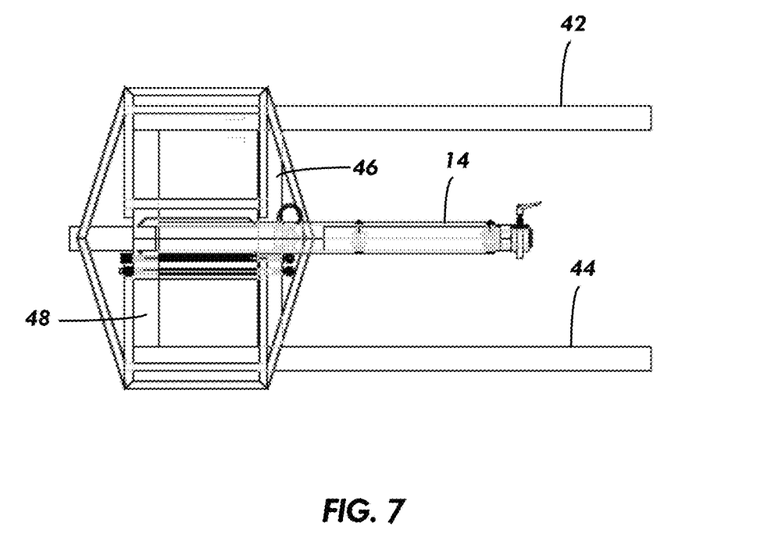
FIG. 7 is a schematic top view of a portable industrial radiography apparatus according to one embodiment of the disclosure.
Figure 8:
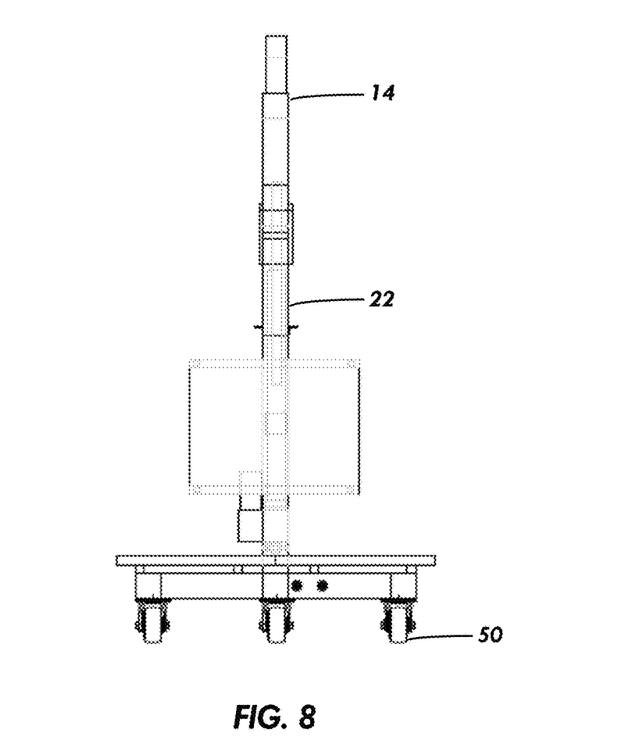
FIG. 8 is a schematic rear view of a portable industrial radiography apparatus according to one embodiment of the disclosure.

Referring now to FIGS. 7 and 8, the support frame 18 includes a first leg 42 and a second leg 44 parallel to the first leg 42. A first cross member 46 and a second cross member 48 extend perpendicular to the first leg 42 and second leg 44 and attach the first leg 42 to the second leg 44. A plurality of casters 50 secured to the support frame 18 allow a user to readily transport the portable radiography apparatus 10 from one location to another. The support frame 18 may include a plurality of feet for further supporting the portable radiography apparatus 10 and to prevent the portable radiography apparatus 10 from moving during an NDT analysis. In another alternative, one or more motors drive the casters 50 such that portable radiography apparatus 10 does not require effort to move, and such that the portable radiography apparatus 10 may be remotely repositioned.

Figure 13:
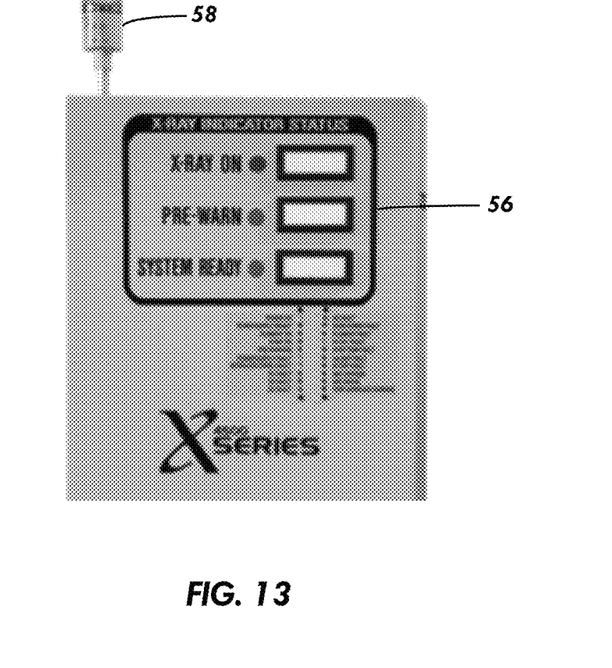
FIG. 13 illustrates visual and diagnostic indicators of a portable industrial radiography apparatus according to one embodiment of the disclosure.

The housing 16 encapsulates the upright support member 22, pivot 24, gusset 26, and other components of the portable radiography apparatus 10 and protects users from contacting moving parts of the portable radiography apparatus 10. Additional components within the housing 16 include a controller and power supply components. The controller may communicate with the linear actuator 28 and actuator 40 for receiving inputs from a remote 52 or other controls and making corresponding adjustments to a position of the x-ray tube 12. The portable radiography apparatus 10 further includes an area alarm that generates an audible alert warning of an impending radiographic examination. Additional diagnostic indicators 56 and a visual indicator 57 on the housing 16 show a status of the portable radiography apparatus 10, such as an active state of the radiography apparatus 10, a ready-state of the apparatus 10, a pre-warning of impending testing, and various color visual alerts from the visual indicator 56 (FIG. 13).

Figure 9:
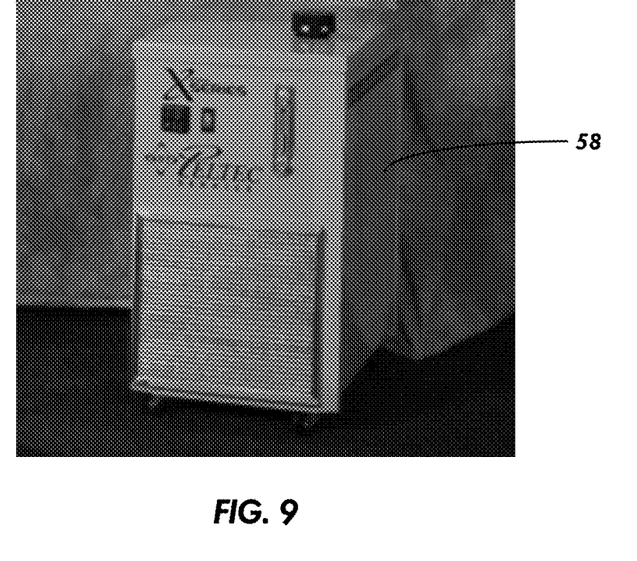
FIG. 9 illustrates an external chiller of a portable industrial radiography apparatus according to one embodiment of the disclosure.
Figure 10:
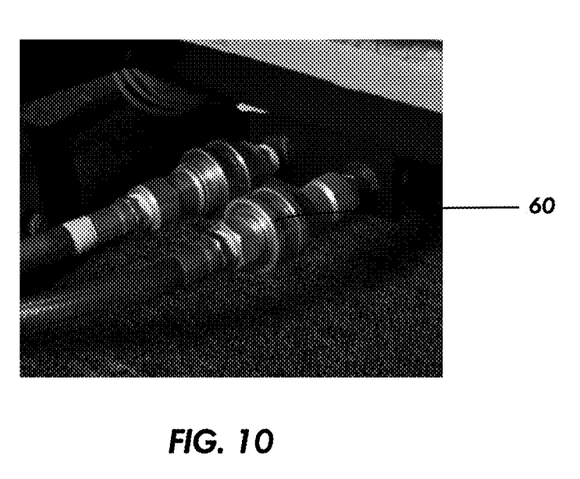
FIG. 10 illustrates a coupler of an external chiller for a portable industrial radiography apparatus according to one embodiment of the disclosure.

The portable industrial radiography apparatus 10 may include an external chiller 58 (FIG. 9) for cooling oil that flows to the x-ray tube 12 when the portable industrial radiography apparatus 10 is operated in warmer environments. Oil from the x-ray tube 12 flows through one or more hoses attached to the external chiller 58 with one or more couplers 60 (FIG. 10). The one or more couplers 60 are preferably quick disconnect couplers such that hoses from the x-ray tube 12 to the external chiller 58 are readily disconnected. The external chiller 58 may include casters such that the external chiller 58 is also portable. Alternatively, the external chiller 58 may be attached to the support frame 18 of the portable industrial radiography device 10.

The portable industrial radiography apparatus 10 allows for easy positioning and adjustment of the x-ray tube 12 adjacent an area of interest for NDT analysis or other examination. Typically, an x-ray tube, such as a 450 kV x-ray tube, may weigh in excess of 200 pounds, thereby making typical positioning and repositioning of the x-ray tube substantially difficult. For example, typical rigging of an x-ray tube requires the use of a crane, forklift, or other equipment to position the x-ray tube.

Figure 11:
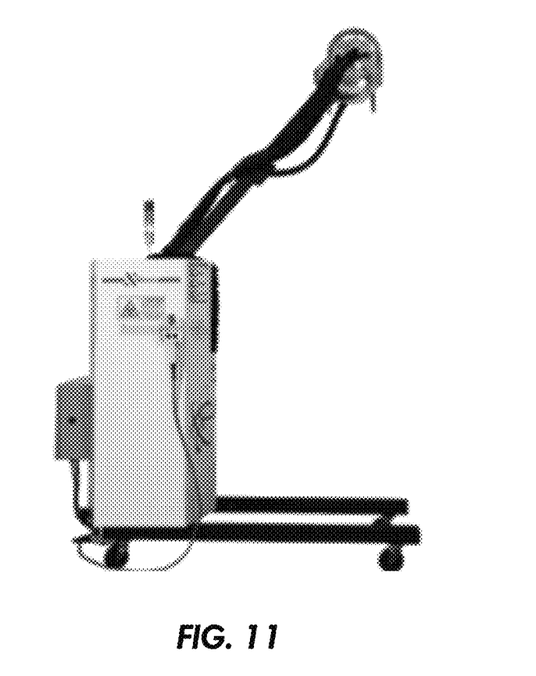
FIGS. 11 and 12 illustrate lift arm positions of a portable industrial radiography apparatus according to one embodiment of the disclosure.
Figure 12:
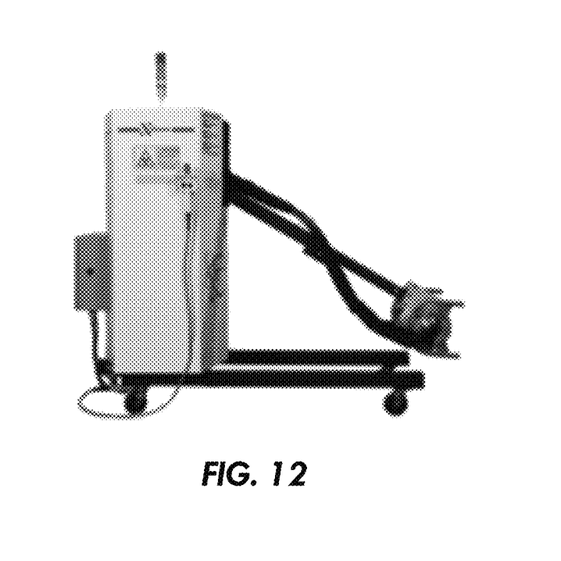

The portable industrial radiography apparatus 10 of the present disclosure provides a compact, robust, and portable device that provides easy manipulation of the x-ray tube 12 around an object of interest. For example, as illustrated in FIGS. 11 and 12, the lift arm 14 is configured to move the x-ray tube 12 such that a height of the x-ray tube 12 is varied relative to a ground surface. The lift arm 14 also adjusts a position of the x-ray tube 12 along a length of the lift arm 14 using the telescoping shaft 30 within the sleeve 32.

Figure 14:
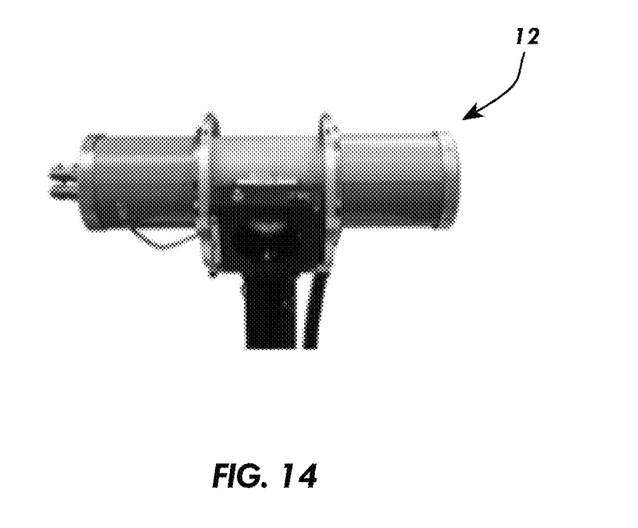
FIG. 14 illustrates an x-ray tube of a portable industrial radiography apparatus according to one embodiment of the disclosure.

In operation, the portable industrial radiography apparatus 10 positions the x-ray tube 12 (FIG. 14) adjacent an object of interest for radiographic NDT analysis. The portable industrial radiography apparatus 10 is positioned near an object of interest. The object of interest may, for example, be placed on a table or other surface as illustrated in FIG. 1. The lift arm 14 raises or lowers the x-ray tube 12, and the telescoping lift arm 14 extends or retracts the x-ray tube 12 along a length of the lift arm 14 until the x-ray tube 12 is maintained in a desired position.

After adjusting the x-ray tube 12 is placed in a desired position, a radiographical analysis of an object of interest is performed. The portable industrial radiography apparatus 10 emits an audible alert when testing occurs, and the visual indicator 56 provides a visual indication of testing in progress. After examining an object of interest, the portable industrial radiography apparatus 10 is repositioned for additional examination or moved away from the object of interest.

The portable industrial radiography apparatus 10 of the present disclosure advantageously provides a compact and robust platform for performing radiographic NDT analysis in an industrial setting. The portable industrial radiography apparatus 10 easily manipulates cumbersome x-ray tubes 12 into various positions for testing, and further allows the portable industrial radiography apparatus 10 to be moved from one area of interest to other areas of interest for additional testing, thereby reducing a need for expensive industrial infrastructure.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A portable industrial radiography apparatus comprising:
   a support frame;
   an upright support member attached to the support frame;
   an elongate lift arm including a first end and a second end, wherein the elongate lift arm is attached to the upright support member at a pivot adjacent the second end of the elongate lift arm;
   an x-ray tube attached to the first end of the elongate lift arm; and
   a linear actuator positioned between the support frame and the elongate lift arm for manipulating a position of the x-ray tube attached to the first end of the elongate lift arm.

2. The portable industrial radiography apparatus of claim 1, wherein the linear actuator is attached to the elongate lift arm at a point between the first end of the elongate lift arm and the pivot.

3. The portable industrial radiography apparatus of claim 1, wherein the elongate lift arm comprises a shaft and a sleeve, wherein the shaft is slidably inserted into the sleeve.

4. The portable industrial radiography apparatus of claim 3, further comprising one or more pairs of opposing angled rollers mounted on the sleeve, wherein the sleeve supports the shaft with the one or more pairs of opposing angled rollers, the one or more pairs of opposing angled rollers shaped to conform to a shape of the shaft.

5. The portable industrial radiography apparatus of claim 4, further comprising a bracket attached to the sleeve, wherein the one or more pairs of opposing angled rollers are attached to the sleeve at the bracket, and wherein the one or more pairs of opposing angled rollers further comprise a fastener extending through each of the one or more pairs of opposing angled rollers to attach the rollers to the bracket.

6. The portable industrial radiography apparatus of claim 4, wherein the shaft and the sleeve have diamond-shaped cross-sectional areas.

7. The portable industrial radiography apparatus of claim 4, further comprising an actuator attached to the elongate lift arm adjacent the second end of the elongate lift arm, wherein the linear actuator urges the shaft in a direction along a length of the elongate lift arm.

8. The portable industrial radiography apparatus of claim 1, further comprising a friction slip ring and set screw positioned between the x-ray tube and the elongate lift arm, wherein the friction slip ring and set screw enable adjustment of the x-ray tube relative to the elongate lift arm.

9. The portable industrial radiography apparatus of claim 1, wherein the upright support member is positioned at an angle of between 5° and 60° relative to a vertical axis.

10. The portable industrial radiography apparatus of claim 9, further comprising a gusset attached between the upright support member and the support frame.

11. The portable industrial radiography apparatus of claim 1, further comprising a housing attached adjacent the upright support member wherein the housing encapsulates the upright support member and the pivot.

12. The portable industrial radiography apparatus of claim 1, wherein the support frame comprises a first leg, a second leg parallel to the first leg, a first cross member extending perpendicular from the first leg to the second leg, and a second cross member parallel to the first cross member.

13. The portable industrial radiography apparatus of claim 1, further comprising an audible area alarm.

14. The portable industrial radiography apparatus of claim 1, further comprising an external chiller, one or more hoses, and a removable coupler, the external chiller in communication with the x-ray tube with the one or more hoses, wherein the one or more hoses are attached to the external chiller with the removable coupler.

15. A portable industrial radiography apparatus comprising:
   a support frame;
   an upright support member attached to the support frame;
   an elongate lift arm including a first end and a second end, wherein the elongate lift arm is attached to the upright support member at a pivot adjacent the second end of the elongate lift arm, the elongate lift arm further comprising:
      a shaft and a sleeve, wherein the shaft is slidably inserted into the sleeve, the shaft and the sleeve having diamond-shaped cross-sectional areas and
      one or more pairs of opposing angled rollers for supporting the shaft within the sleeve;
   an x-ray tube attached to the first end of the elongate lift arm; and
   a linear actuator positioned between the support frame and the elongate lift arm for manipulating a position of the x-ray tube attached to the first end of the elongate lift arm.

16. The portable industrial radiography apparatus of claim 15, further comprising an actuator attached to the elongate lift arm adjacent the second end of the elongate lift arm, wherein the linear actuator urges the shaft in a direction along a length of the elongate lift arm.

17. The portable industrial radiography apparatus of claim 15, wherein the shaft and the sleeve have diamond-shaped cross-sectional areas.

18. The portable industrial radiography apparatus of claim 15, further comprising a friction slip ring and set screw adjacent the x-ray tube.

19. The portable industrial radiography apparatus of claim 15, wherein the upright support member is positioned at an angle of between 5° and 60° relative to a vertical axis.

20. A portable industrial radiography apparatus comprising:
   a support frame including a first leg, a second leg parallel to the first leg, a first cross member extending perpendicular from the first leg to the second leg, and a second cross member parallel to the first cross member;
   an upright support member attached to the support frame, the upright support member positioned at an angle of between 5° and 60° relative to a vertical axis;
   an elongate lift arm including a first end and a second end, wherein the elongate lift arm is attached to the upright support member at a pivot adjacent the second end of the elongate lift arm, the elongate lift arm further comprising:
      a shaft and a sleeve, wherein the shaft is slidably inserted into the sleeve, the shaft and the sleeve having diamond-shaped cross-sectional areas,
      one or more pairs of opposing angled rollers for supporting the shaft within the sleeve, and
      an actuator attached to the elongate lift arm adjacent the second end of the elongate lift arm, wherein the actuator urges the shaft in a direction along a length of the elongate lift arm;

an x-ray tube, a friction slip ring, and a set screw, the x-ray tube attached to the first end of the elongate lift arm adjacent the friction slip ring and the set screw; and a linear actuator positioned between the support frame and the elongate lift arm for manipulating a position of the x-ray tube attached to the first end of the elongate lift arm.

* * * * *

UNITED STATES PATENT AND TRADEMARK OFFICE
CERTIFICATE OF CORRECTION

PATENT NO.        : 10,151,710 B2
APPLICATION NO.   : 14/803369
DATED             : December 11, 2018
INVENTOR(S)       : Richard Pellechia It is certified that error appears in the above-identified patent and that said Letters Patent is hereby corrected as shown below:

On the Title Page

Delete the title page and substitute therefore with the attached title page consisting of the corrected illustrative figure(s).

In the Drawings

Please replace FIGS. 1-14 with FIGS. 1-14 as shown on the attached pages.

Signed and Sealed this
Third Day of December, 2019

Andrei Iancu
*Director of the United States Patent and Trademark Office*

(12) United States Patent
Pellechia

(10) Patent No.: US 10,151,710 B2
(45) Date of Patent: Dec. 11, 2018

(54) PORTABLE INDUSTRIAL RADIOGRAPHY APPARATUS

(71) Applicant: Peltec Services, Inc., Darlington, SC (US)

(72) Inventor: Richard Pellechia, Florence, SC (US)

(*) Notice: Subject to any disclaimer, the term of this patent is extended or adjusted under 35 U.S.C. 154(b) by 0 days.

(21) Appl. No.: 14/803,369

(22) Filed: Jul. 20, 2015

(65) Prior Publication Data
US 2016/0021725 A1   Jan. 21, 2016

Related U.S. Application Data

(60) Provisional application No. 62/026,160, filed on Jul. 18, 2014.

(51) Int. Cl.
*G01N 23/04* (2018.01)
*G01N 23/06* (2018.01)
*G01N 23/083* (2018.01)
*G01N 23/087* (2018.01)
*H05G 1/02* (2006.01)

(52) U.S. Cl.
CPC ........ *G01N 23/04* (2013.01); *G01N 23/06* (2013.01); *G01N 23/083* (2013.01); *G01N 23/087* (2013.01); *G01N 2223/301* (2013.01); *G01N 2223/308* (2013.01); *H05G 1/025* (2013.01)

(58) Field of Classification Search
CPC ....... A61B 6/4405; A61B 6/44; A61B 6/4411; A61B 6/4429; A61B 6/4452; A61B 6/4458; G01N 23/04; G01N 23/06; G01N 23/083; G01N 23/087

USPC ............. 378/196–198, 51, 53–55, 58, 62
See application file for complete search history.

(56) References Cited

U.S. PATENT DOCUMENTS

| | | | | |
|---|---|---|---|---|
| 1,877,690 A | * | 9/1932 | Russell | A61B 6/14 248/174 |
| 2,232,014 A | * | 2/1941 | Simon | A61B 6/447 378/190 |
| 2,360,036 A | * | 10/1944 | Boucher | G01N 23/18 378/201 |
| 2,588,124 A | * | 3/1952 | Kizaur | A61B 6/00 378/177 |
| 2,607,012 A | * | 8/1952 | Siebert | G01M 3/005 248/292.13 |
| 3,644,735 A | * | 2/1972 | Vandervelden | A61B 6/14 378/197 |
| 3,790,805 A | | 2/1974 | Foderaro | |
| 4,166,602 A | * | 9/1979 | Nilsen | A61B 6/447 248/280.11 |
| 4,202,355 A | * | 5/1980 | Loeffler | A61B 5/107 600/587 |

(Continued)

*Primary Examiner* — Allen C. Ho
(74) *Attorney, Agent, or Firm* — Matthew M. Googe; Robinson IP Law, PLLC

(57) ABSTRACT

A portable industrial radiography apparatus is provided for radiographic non-destructive testing. The portable industrial radiography apparatus includes a support frame, an upright support member attached to the support frame, an elongate lift arm including a first end and a second end, wherein the elongate lift arm is pivotally attached to the upright support member adjacent the second end of the lift arm, an x-ray tube attached to the first end of the elongate lift arm, and a linear actuator positioned between the support frame and the lift arm for manipulating a position of the x-ray tube attached to the first end of the elongate lift arm.

20 Claims, 9 Drawing Sheets

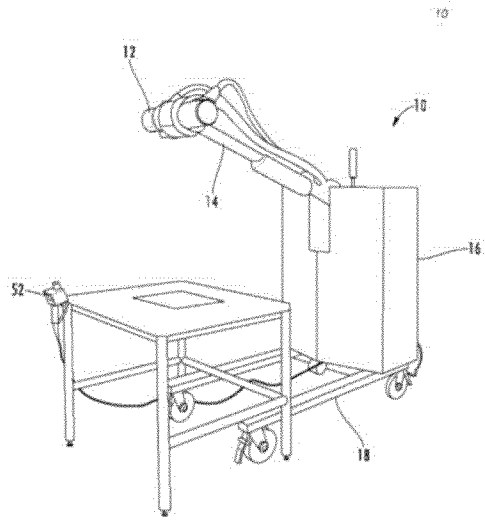

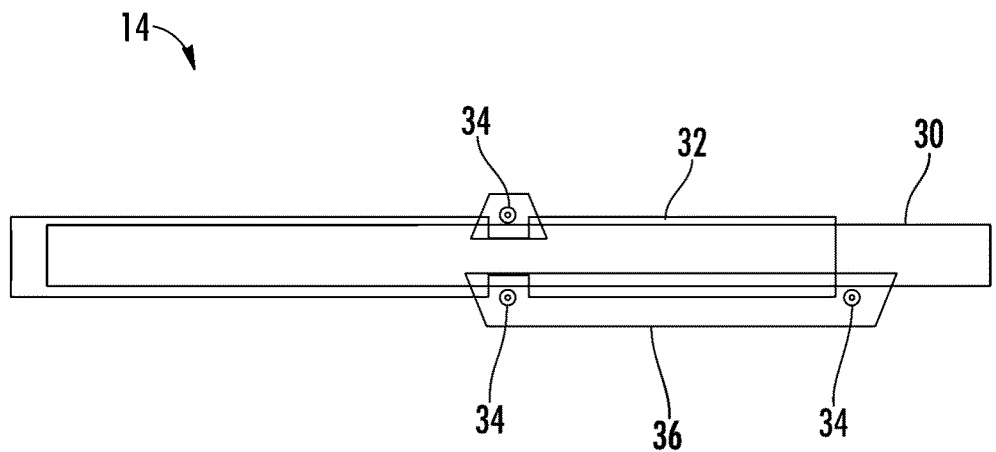
FIG. 5
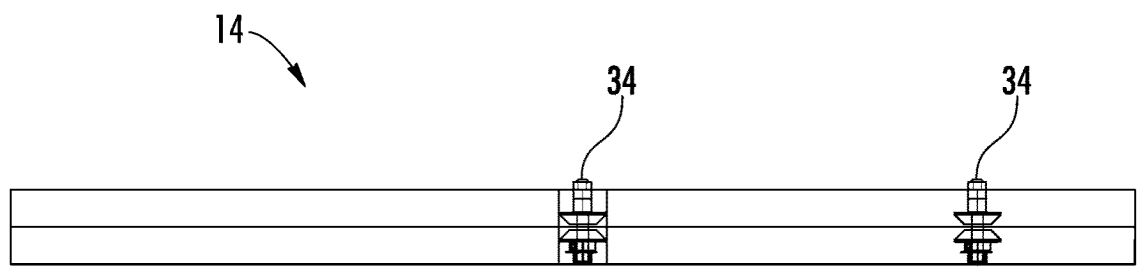
FIG. 6

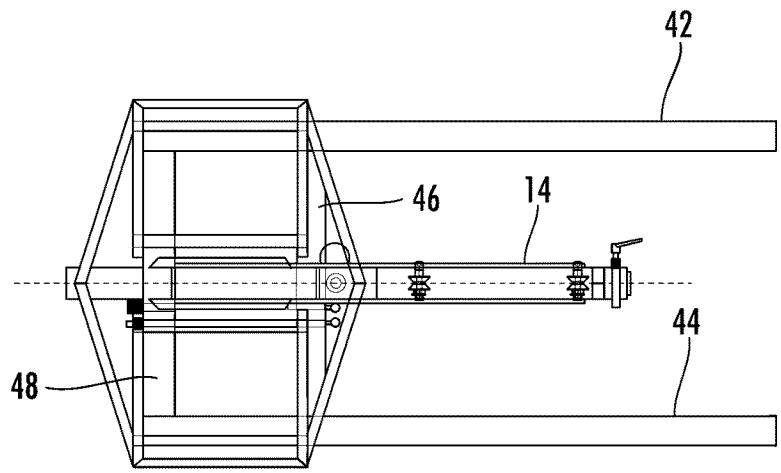
FIG. 7
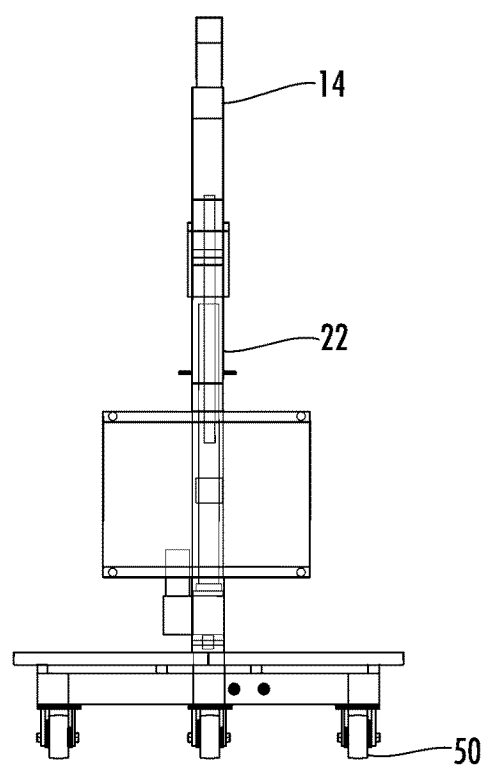
FIG. 8

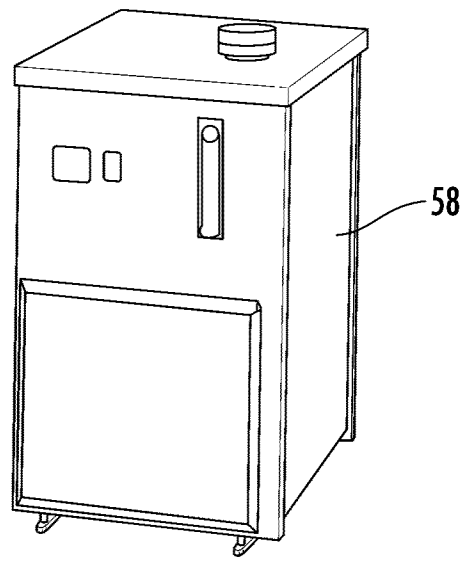
FIG. 9
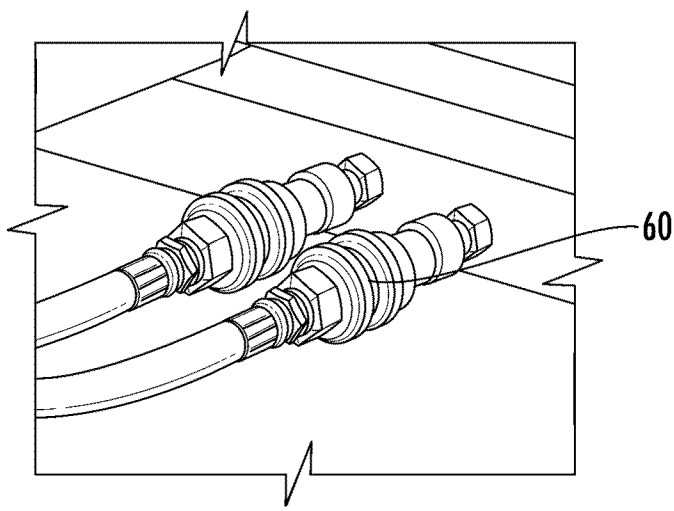
FIG. 10

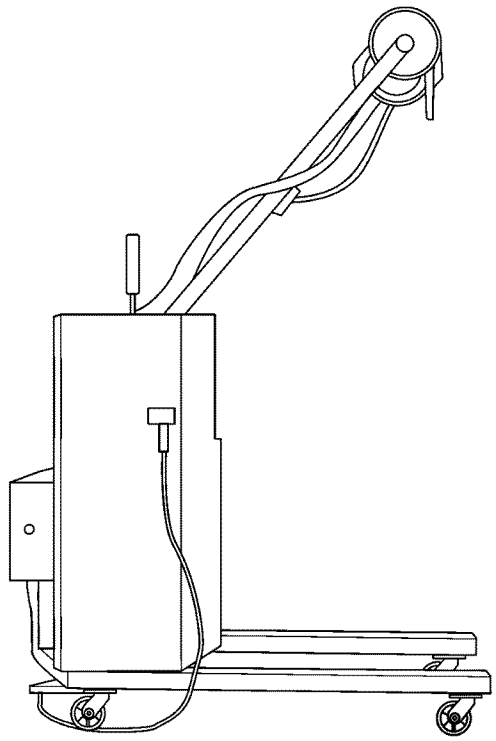
FIG. 11
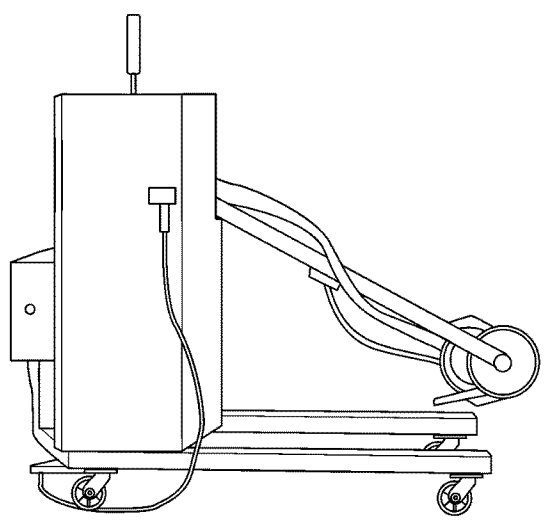
FIG. 12

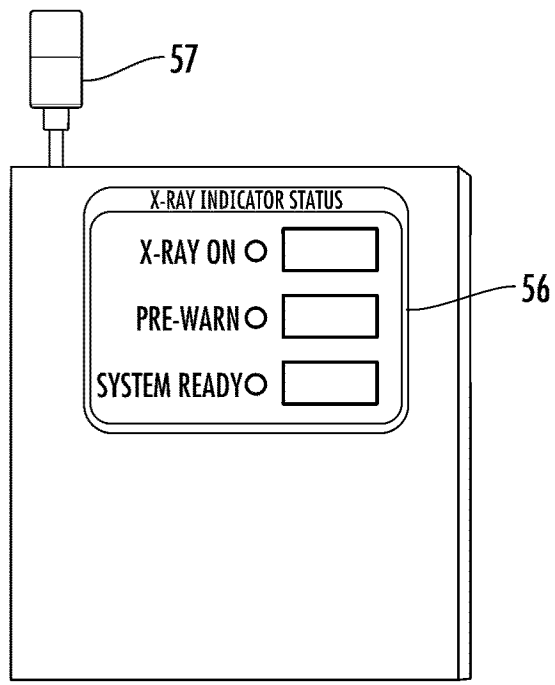
FIG. 13
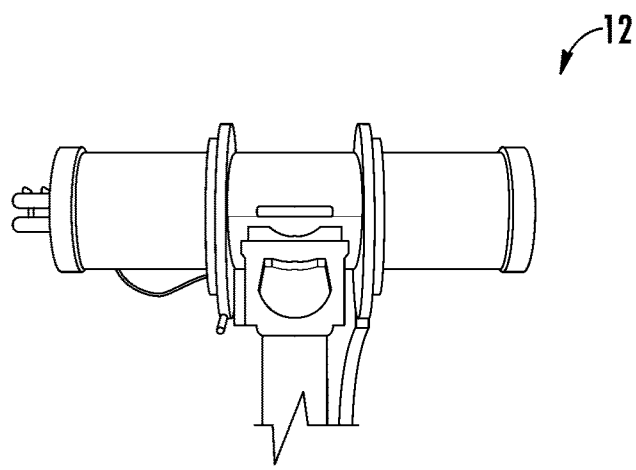
FIG. 14